United States Patent [19]
Haber et al.

[11] Patent Number: 5,281,198
[45] Date of Patent: Jan. 25, 1994

[54] PHARMACEUTICAL COMPONENT-MIXING DELIVERY ASSEMBLY

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 878,384

[22] Filed: May 4, 1992

[51] Int. Cl.⁵ .............................................. A61M 37/00
[52] U.S. Cl. ..................................... 604/86; 604/191; 604/201; 604/209; 604/232
[58] Field of Search .............................. 604/82, 85–91, 604/191, 200–205, 207–209, 232, 234

[56] References Cited

U.S. PATENT DOCUMENTS

| | | | |
|---|---|---|---|
| 4,055,177 | 10/1977 | Cohen | 604/88 |
| 4,693,706 | 9/1987 | Ennis, III | 604/87 |
| 4,755,169 | 7/1988 | Sarnoff et al. | 604/51 |
| 4,886,495 | 12/1989 | Reynolds | 604/88 |
| 5,041,088 | 8/1991 | Ritson et al. | 604/88 |
| 5,092,843 | 3/1992 | Monroe et al. | 604/138 |
| 5,114,411 | 5/1992 | Haber et al. | 604/203 |

Primary Examiner—C. Fred Rosenbaum
Assistant Examiner—Corrine Maglione
Attorney, Agent, or Firm—Townsend and Townsend Khourie and Crew

[57] ABSTRACT

A pharmaceutical component-mixing syringe assembly (2) is particularly suited for packaging, reconstituting and dispensing a series of equal doses of a multiple component pharmaceutical, such as human growth hormone reconstituted from a diluent component (128) and a lyophilized component (34). The pharmaceutical components are contained within first and second cartridges (10, 36) of the type having a movable piston (12, 40). The second cartridge is forced into the interior of the first cartridge causing a spike assembly (132) between the two to fluidly couple the two cartridges and drive the piston of the first cartridge into the first cartridge causing the contents of the first cartridge to be driven into the second cartridge, thereby mixing. A reciprocating ratchet plunger (104) is used to drive the second piston. The distance the ratchet plunger moves, and thus the dose, is determined by the position of a user-inaccessible dosing key stop (116) along the length of the ratchet plunger.

19 Claims, 6 Drawing Sheets

5,281,198

PHARMACEUTICAL COMPONENT-MIXING DELIVERY ASSEMBLY

BACKGROUND OF THE INVENTION

Some pharmaceuticals, such as human growth hormone, are supplied as two components, typically a lyophilized component and a diluent. The two components are often mixed prior to use because of the relatively short shelf life of the pharmaceutical when in its liquid state. Another problem with human growth hormone is its expense. It is a very expensive pharmaceutical so that the dosage must be very closely controlled both from the point of not over or underdosing the patient and also to keep from wasting expensive pharmaceutical.

SUMMARY OF THE INVENTION

The present invention is directed to a pharmaceutical component mixing syringe assembly especially suited for use with two component pharmaceuticals, including a lyophilized component and a diluent, such as human growth hormone. The invention provides a package for the two pharmaceutical components, a reconstituting tool for the components, and a programmable, multiple dose syringe by which repeated doses of the same, chosen dose can be given.

The pharmaceutical components are contained within first and second pharmaceutical-containing cartridges of the type having a movable piston housed within the cartridge barrels. The cartridges are housed within a common housing, typically the syringe barrel, with the needle end of the second cartridge opposite the plunger end of the first cartridge. The first cartridge preferably has a larger diameter than the second cartridge to allow the second cartridge to pass through the plunger end of the first cartridge. A spike assembly is preferably used between the two cartridges so that forcing the second cartridge into the first cartridge causes the spike assembly to pierce the septum covering the needle end of the second cartridge and the piston in the first cartridge. The spike assembly is constructed so that the double ended needle pierces the septum of the second cartridge before it pierces the piston of the first cartridge to insure that the diluent from the first cartridge does not leave the first cartridge until the spike has passed into the second cartridge. Continued movement of the second cartridge into the first cartridge forces the contents of the first cartridge through the double ended needle and into the second cartridge.

The second cartridge is preferably mounted within and carried by an activation sleeve which itself slides axially within the syringe barrel. To activate the syringe assembly and thus cause the two components to mix within the second cartridge, the activation sleeve is pushed axially into the syringe barrel carrying the second cartridge therewith, thus forcing a second cartridge into the interior of the first cartridge. This causes the spike assembly to fluidly couple the two cartridges and drive the piston of the first cartridge towards the needle end of the first cartridge so that the contents of the first cartridge are driven into the second cartridge, thereby mixing.

A drive stem is mounted with its distal end adjacent the piston of the second cartridge. A reciprocating, one-way drive stem driver is used to drive the drive stem against the second piston to force the mixed pharmaceutical in the second cartridge through the needle assembly during an injection. This is preferably accomplished by forcing the mixed pharmaceutical through the spike assembly and out through the needle assembly mounted to the needle end of the first cartridge.

The drive stem driver preferably includes first and second ratchets. The first ratchet is mounted at a fixed position within the activation sleeve adjacent the plunger end of the second cartridge. The first ratchet permits the drive stem to move towards the second piston, that is in a distal direction, but not in the opposite direction. The second ratchet is mounted to a user-operated ratchet plunger. The second ratchet slides over the drive stem when the ratchet plunger is pulled in the proximal direction, but engages and drives the drive stem in the distal direction when the ratchet plunger is driven in the distal direction. Thus, reciprocating movement of the ratchet plunger by the user causes the drive stem to be moved only during the distal movement of the ratchet plunger and thus during an injection stroke.

The distance the ratchet plunger moves may be determined by the position of a dosing key stop along the length of the ratchet plunger. The dosing key stop determines the length of stroke of the ratchet plunger and thus the volume of the dose. The dosing key stop is positioned at a chosen position along the ratchet plunger by the physician or pharmacist according to the dose of the pharmaceutical to be administered. After so positioning, the ratchet plunger, with the dosing key stop mounted at the chosen position, is inserted into the proximal end of the activation sleeve.

The proximal end of the activation sleeve is slit axially to allow it to dilate to permit the dosing key stop to be inserted into the interior of the activation sleeve. Once inserted, the ratchet plunger cannot be removed from the activation sleeve and the dosing key stop cannot be repositioned.

The ratchet plunger is connected to the second ratchet, typically through a bayonet type of connection between a ratchet plunger and the second ratchet.

One of the primary advantages of the invention is its simplicity. Multiple functions, including packaging the pharmaceutical components, reconstituting the components, and delivery of multiple pre-set dosages of the mixed pharmaceutical, is provided by a relatively simple assembly. After the dose has been set by the physician or pharmacist, no adjustments need to be done by the user. The ratchet plunger is merely pulled back as far as it will go in the proximal direction and then depressed fully during the injection to achieve the proper dose. By making the dosing key stop inaccessible to the user, modification of the dose by the user can be effectively eliminated.

Other features and advantages of the invention will appear from the following description in which the preferred embodiment has been set forth in detail in conjunction with the accompanying drawings.

DESCRIPTION OF THE PREFERRED EMBODIMENT

Figure 1:
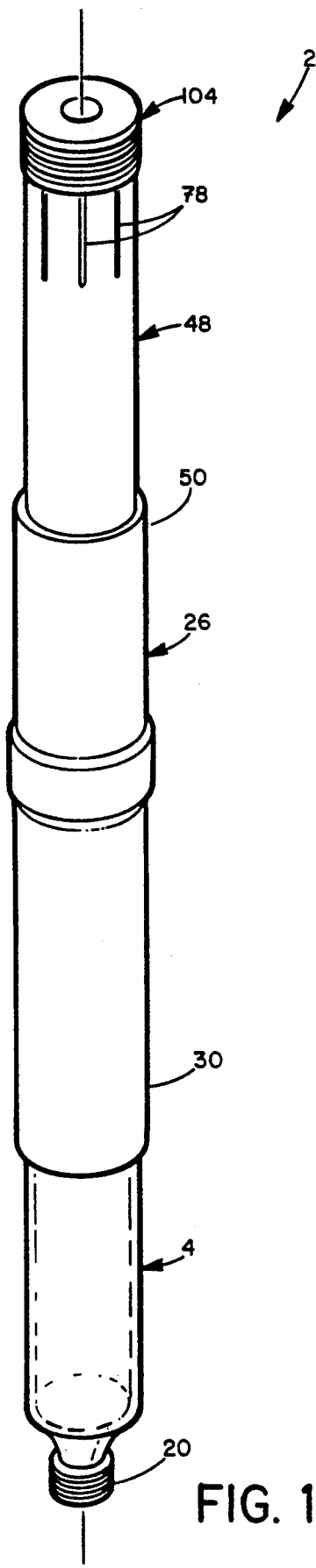
FIG. 1 is an isometric view of a syringe assembly made according to the invention.
Figure 2:
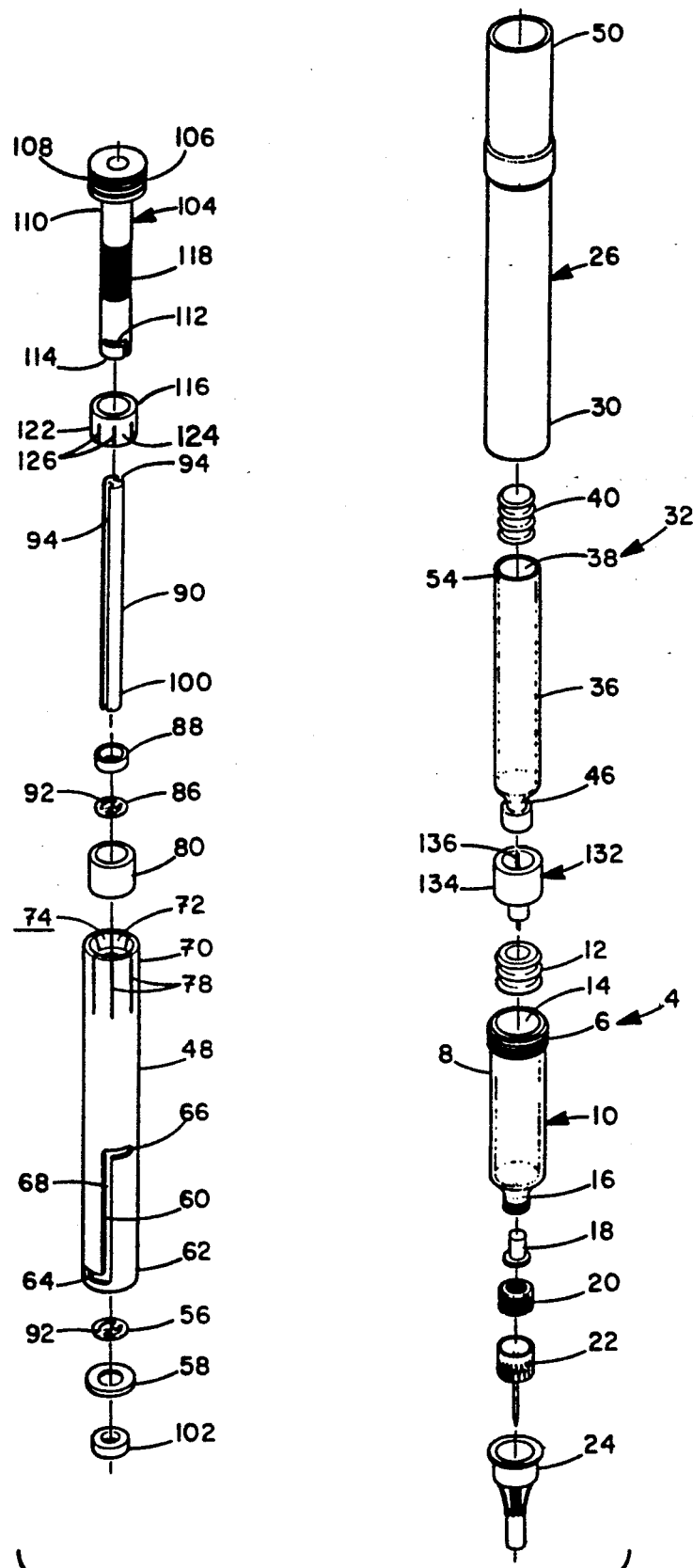
FIG. 2 is a exploded isometric view of the syringe assembly of FIG. 1, including a needle assembly and a sheath.
Figure 3:
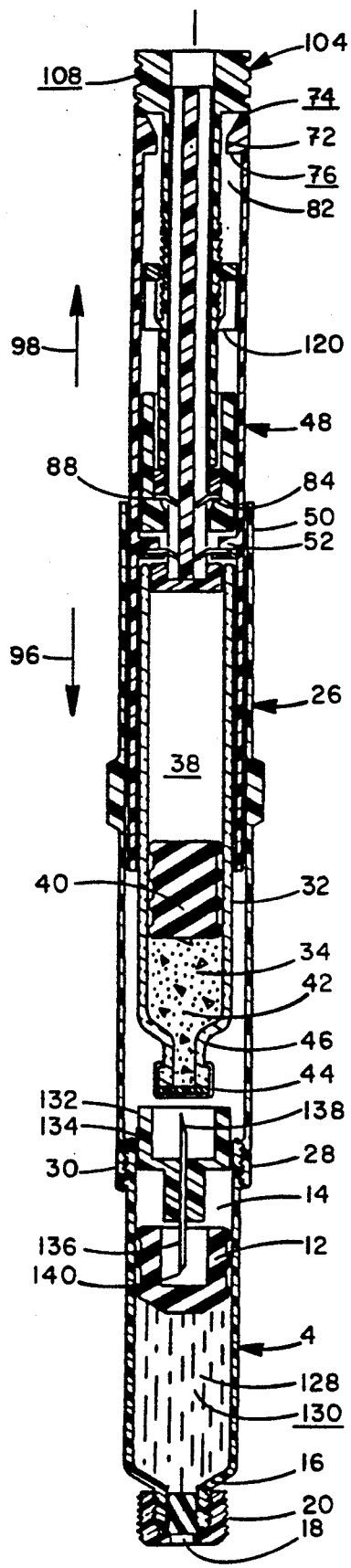
FIG. 3 is a cross-sectional view of the syringe assembly of FIG. 1 with the cartridges in their pre-mixed position after the ratchet plunger has been inserted into the activation sleeve.
Figure 6:
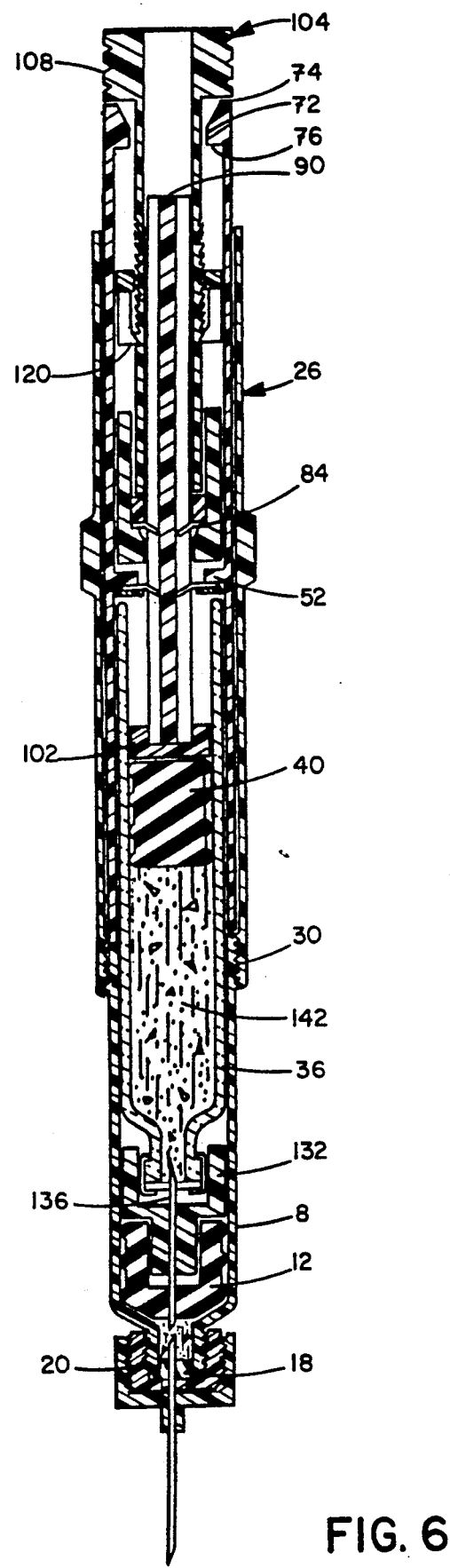
FIG. 6 shows the syringe assembly of FIG. 5 following an injection with a needle assembly mounted to the needle end of the first cartridge and the ratchet plunger pushed in the distal direction to the post-inject position.

FIGS. 1-3 illustrate a pharmaceutical component-mixing syringe assembly 2 in assembled and exploded isometric views. Assembly 2 includes a first, diluent cartridge 4 having a set of external threads 6 at the proximal or plunger end 8 of a barrel 10. Cartridge 4 also includes a piston 12 housed within the interior 14 of barrel 10. The distal or needle end 16 of cartridge 4 has an extended elastomeric septum 18 secured thereto by a nose cap 20. Nose cap 20 has internal threads for mounting to needle end 16 and external threads to permit a double-ended needle assembly 22 to be secured to needle end 16 of cartridge 4 as shown in FIG. 6. When secured thereto, needle assembly 22 can be covered with a protective sheath 24.

Syringe assembly 2 also includes a syringe barrel 26 having internal threads 28 at a distal end 30 sized to engage external threads 6 of barrel 10. Threads 6, 28 permit cartridge 10 to be fixed to distal end 30 of syringe barrel 26.

A second cartridge 32, which contains a lyophilized pharmaceutical 34, includes a barrel 36 having a hollow interior 38 which houses a second piston 40. Lyophilized pharmaceutical 34 is contained within a variable volume region 42 between piston 40 and an elastomeric septum 44 at the distal or needle end 46 of cartridge 32. Cartridge 32 is mounted within an activation sleeve 48 which extends from the proximal end 50 of syringe barrel 26. Activation sleeve 48 has an inner annular ledge 52, see FIG. 3, positioned about half-way along its length. Barrel 36 of cartridge 32 fits snugly within the interior of activation sleeve 48 with the proximal end 54 of second cartridge 32 generally abutting annular ledge 52. However, as shown in FIG. 3, a first ratchet disc 56 and a support washer 58 are captured between proximal end 54 and ledge 52; the purpose of these elements will be described below.

Activation sleeve 48 has a generally Z-shaped slot 60 formed along its length towards the distal end 62 of sleeve 48. Slot 60 engages a pin (not shown) extending inwardly from the interior of syringe barrel 26. Slot 60 includes a shipping position region 64 towards distal end 62 and a post-mixed region 66 away from distal end of 62, regions 64, 66 connected by an axially extending region 68. The engagement of the pin extending inwardly from syringe barrel 26 into slot 60 controls the movement of activation sleeve 48, and second cartridge 32 therewith, within syringe barrel 26. With the cartridges in the pre-mixed position, as occurs during shipping, the pin is engaged in shipping position region 64 so that an axial force on activation sleeve 48 tending to collapse activation sleeve into syringe barrel 26 is prevented. Preferably regions 64, 66 both include some type of detent to keep the pin engaged within the respective regions 64, 66.

Activation sleeve 48 includes a proximal end 70, having an inwardly extending rim 72. Rim 72 has an outwardly facing tapered surface 74 and a radially extending, inwardly facing surface 76. End 70 has a number of axially extending slits 78 which permit end 70 to dilate to permit the introduction of a ratchet collar 80 into the interior 82 of activation sleeve 48 through proximal end 70. Ratchet collar 80 includes a ledge 84 against which a second ratchet disc 86 is positioned. Ratchet disc 86 is secured in place by a collar 88 press fit into ratchet collar 80.

A drive stem 90 is mounted within activation sleeve 48 and passes through and is engaged by first and second ratchet discs 56, 86. Ratchet discs 56, 86 have pairs of angled ratcheting fingers 92 which engage axially extending slots 94 formed in drive stem 90. Ratchet disc 56, which is fixed in place relative to sleeve 48, permits drive stem 90 to move in a distal direction 96, but not in a proximal direction 98. Movement of drive stem 90 in distal direction 96 causes the distal end 100 of drive stem 90 to press against a stopper plate 102 positioned within interior 38 of barrel 36. See FIG. 3.

A ratchet plunger 104 is used to administer the dose of the mixed pharmaceutical, as will be discussed below. Ratchet plunger 104 has an enlarged outer end 106 with a grooved outer surface 108 to allow ratchet plunger 104 to be grasped by the user. Ratchet plunger 104 also includes an axially extending shaft 110 having a bayonet slot 112 at a distal end 114 thereof. Slot 112 is used to engage an inwardly extending lug (not shown) formed on the inside of ratchet collar 80 to secure ratchet collar 80, second ratchet disc 86 and collar 88 to ratchet plunger 104. This is accomplished through a twist lock movement upon insertion of ratchet plunger 104 through proximal end 70 of activation sleeve 48.

Figure 4:
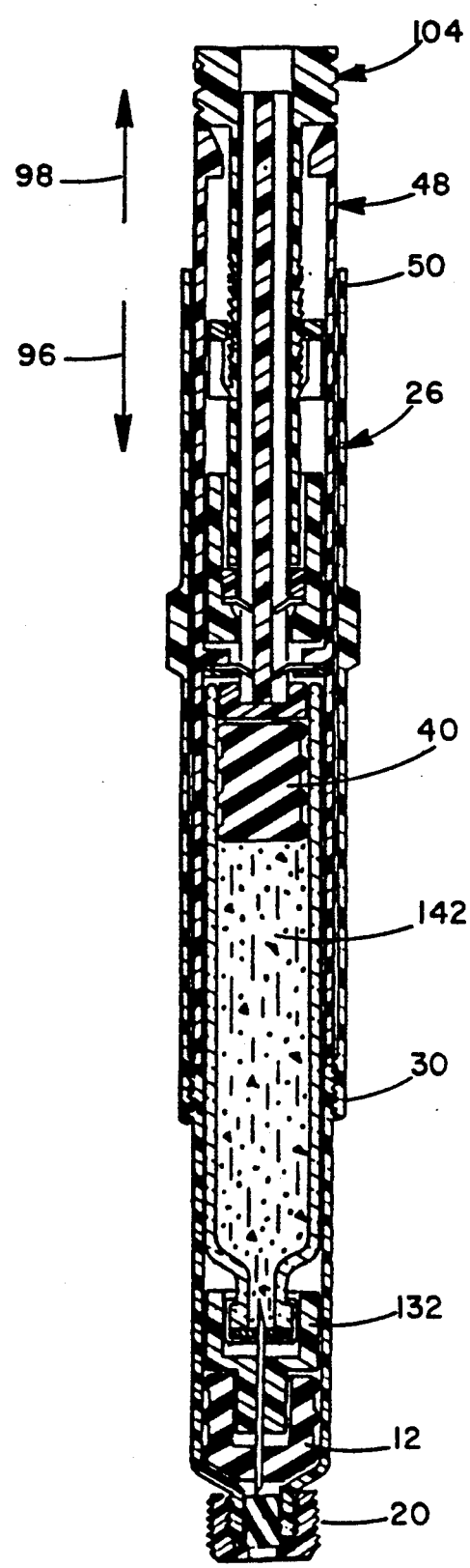
FIG. 4 illustrates the syringe assembly of FIG. 3 with the cartridges in their post-mixed position following mixing of the pharmaceutical components in the second cartridge.

The length of the reciprocal axial movement of ratchet plunger 104 is determined by the axial position of a dosing key stop 116 along the length of shaft 110. Shaft 110 has a serrated region 118 engaged by the inwardly extending teeth 120 formed at the distal end 122 of dosing stop 116. Distal end 122 is divided into a number of spring fingers 124 by making a number of axially extending slits 126 and dosing stop 116. This allows spring fingers 124 to dilate and engage serrated region 118. The individual grooves of serrated region 118 are formed so that the position of dosing key stop 116 along shaft 110 is chosen, such as by a physician or pharmacist, by moving the dosing key stop in the proximal direction 98 until the chosen position is achieved. As can be seen by comparing FIGS. 4 and 5, the distance 128 ratchet plunger 104 can move axially within activation of sleeve 48 is determined by the position of dosing key stop 116 along shaft 110. When ratchet plunger 104 is the pre-injection position of FIG. 5, further movement of ratchet plunger 104 in proximal direction 98 is halted by the engagement of dosing key stop 116 with surface 76.

Prior to syringe assembly 2 being provided to the patient, the physician or pharmacist locates dosing key stop 116 at the proper, chosen position along shaft 110 according to the dose needed. The physician or pharmacist then inserts ratchet plunger 104, together with dosing key stop 116, through proximal end 70 of activation sleeve 48. This is possible because dosing key stop 116 engages tapered surface 74, thus causing proximal end 70 to dilate and then spring back to the position of FIG. 3 after the dosing key stop has cleared surface 76. Once in the assembled condition of FIG. 3, the user is prevented from changing the dose by changing the position of dosing key stop 116 along shaft 110.

To mix lyophilized pharmaceutical 34 with diluent 128 housed within the variable volume region 130 formed between extended septum 18 and piston 12, the user grasps activation sleeve 48 and twists it in a clockwise direction relative to syringe barrel 26 to permit the pin extending inwardly from within barrel 26 into slot 60 to move out of region 64 and into region 68. The user then presses on ratchet plunger 104, thus driving ratchet plunger 104, activation sleeve 48 and second cartridge 32 in the distal direction 96 from the pre-mixed position of FIG. 3 to the post-mixed position of FIG. 4. Doing so causes needle end 46 of second cartridge 32 to drive a spike assembly 132 towards piston 12.

Spike assembly 132 includes a spike carrier 134 and a double-ended hollow spike 136. The proximal end 138 is sharper than the distal end 140 of spike 136. This ensures that proximal end 138 will pierce septum 44 before distal end 140 passes through piston 12. Otherwise, if spike 136 were to pass through piston 12 and enter region 130 prior to proximal end 138 entering region 42, diluent 128 could be driven into the region external of second cartridge 32.

Continued movement of second cartridge 32 in distal direction 96 drives spike assembly 132 against piston 12, causing piston 12 to move towards needle end 16 of first cartridge 10. At the end of the movement, that is with the cartridges in the post-mixed position of FIG. 4, activation sleeve 48 is again twisted in a clockwise direction relative to syringe barrel 26 so that the pin extending from the interior of the syringe barrel into slot 60 enters region 66 to secure activation sleeve 48, and thus second cartridge 32, in place.

Figure 5:
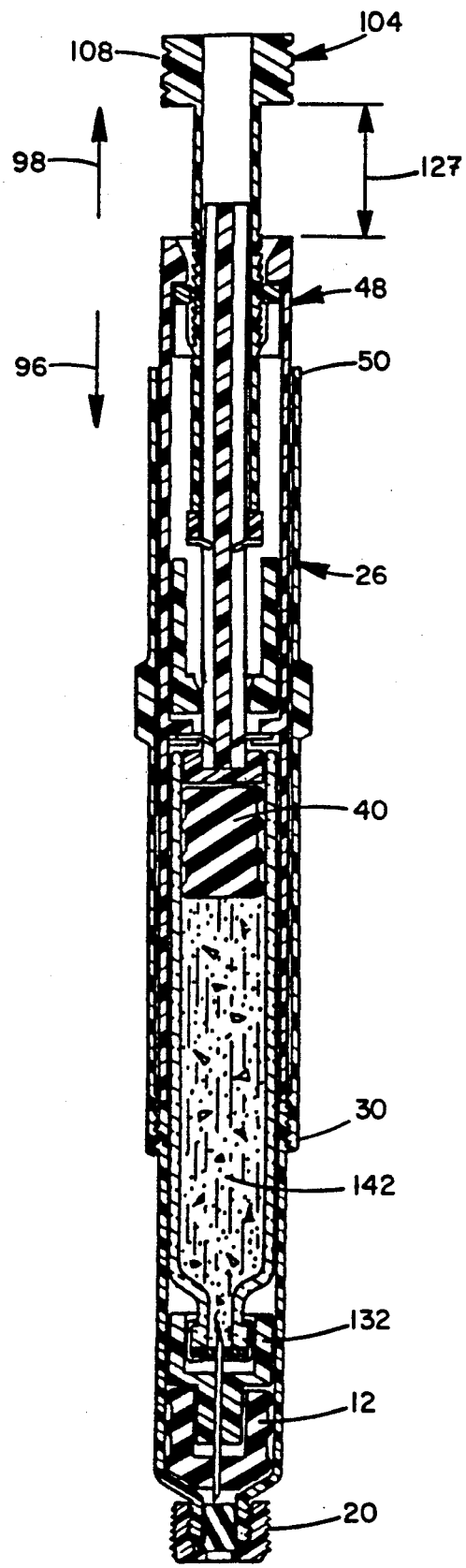
FIG. 5 is a cross-sectional view of the syringe assembly of FIG. 4 showing the ratchet plunger pulled in the proximal direction to the pre-inject position.

To dispense a dose of mixed pharmaceutical 142, the user mounts needle assembly 22 to nose cap 20, see FIG. 6, pulls ratchet plunger in the proximal direction 98 as shown in FIG. 5 to the pre-inject position. Mixed pharmaceutical 142 is then dispensed by pressing on ratchet plunger 104 in the distal direction 96 causing ratchet plunger 104 to move distance 127. Doing so causes second ratchet disc 86 to engage drive stem 90 and force drive stem 90 in distal direction 96 the same distance 127, thus forcing stopper plate 102 and piston 40 distance 127 until ratchet plunger 104 is in the post-inject position of FIG. 6. Since a repeat of the reciprocal movement of ratchet plunger 104 does not allow drive stem 90 to move in proximal direction 98, each cycle or reciprocation of the ratchet plunger causes second piston 40 to move the same distance, thus dispensing the same dose of mixed pharmaceutical 142.

Modification and variation can be made to the disclosed embodiment without departing from the subject of the invention, as defined in the following claims. For example, first cartridge 10 is preferably a specialized cartridge having external threads 6 for mounting to distal end 30 of syringe barrel 26. A conventional cartridge could be used as well by using an adapter to secure the conventional cartridge to syringe barrel 26.

What is claimed is:

1. A pharmaceutical component-mixing delivery assembly comprising:
   first and second cartridges including needle ends, plunger ends, interiors and pistons within the interiors, the first and second cartridges containing first and second pharmaceutical components within first and second variable volume regions defined between the needle ends and the pistons;
   means for housing the first and second cartridges, the first and second cartridges being movable relative to one another from a pre-mixed position to a post-mixed position;
   means for driving the first pharmaceutical component from the first variable volume region into the second variable volume region to create a mixed pharmaceutical when the cartridges are moved to the post-mixed position;
   means for accessing the mixed pharmaceutical; and
   reciprocating means for forcing first and second predetermined amounts of the mixed pharmaceutical through the accessing means by driving the piston of the second cartridge a distance during first and second strokes of the reciprocating means, the first and second predetermined amounts having approximately the same volume.

2. The delivery assembly of claim 1 wherein the first pharmaceutical is a diluent and the second pharmaceutical is a lyophilized pharmaceutical component.

3. A pharmaceutical component-mixing delivery assembly comprising:
   first and second cartridges including needle ends, plunger ends, interiors and pistons within the interiors, the first and second cartridges containing first and second pharmaceutical components within first and second variable volume regions defined between the needle ends and the pistons, the first and second cartridges being sized so that the needle end of the second cartridge can pass into the first cartridge through the plunger end of the first cartridge;
   housing means for housing the first and second cartridges, the first and second cartridges being movable relative to one another from a pre-mixed position to a post-mixed position;
   means for driving the first pharmaceutical component from the first variable volume region into the second variable volume region to create a mixed pharmaceutical when the cartridges are moved to the post-mixed position;
   means for accessing the mixed pharmaceutical; and
   reciprocating means for forcing first and second predetermined amounts of the mixed pharmaceutical through the accessing means by driving the piston of the second cartridge a distance during first and second strokes of the reciprocating means, the first and second predetermined amounts having approximately the same volume.

4. The delivery assembly of claim 3 wherein the driving means includes:
   spike means for fluidly coupling the first and second variable volume regions; and
   means for forcing the piston of the first cartridge towards the needle end of the first cartridge by forcing the needle end of the second cartridge into the first cartridge and towards the needle end of the first cartridge.

5. A pharmaceutical component-mixing delivery assembly comprising:
   first and second cartridges including needle ends, plunger ends, interiors and pistons within the interiors, the first and second cartridges containing first and second pharmaceutical components within first and second variable volume regions defined between the needle ends and the pistons;

housing means for housing the first and second cartridges, the first and second cartridges being movable relative to one another from a pre-mixed position to a post-mixed position;

means for driving the first pharmaceutical component from the first variable volume region into the second variable volume region to create a mixed pharmaceutical when the cartridges are moved to the post-mixed position;

means for accessing the mixed pharmaceutical; and reciprocating means for forcing first and second predetermined amounts of the mixed pharmaceutical through the accessing means by driving the piston of the second cartridge a distance during first and second strokes of the reciprocating means, the first and second predetermined amounts having approximately the same volume, the reciprocating forcing means also including a reciprocating ratchet plunger having a length, and a dosing key stop mounted to the plunger at a chosen position along the length, the chosen position corresponding to said distance the piston of the second cartridge moves during each stroke.

6. The delivery assembly of claim 5 wherein the reciprocating forcing means includes means for preventing a user from changing said chosen position.

7. A pharmaceutical component-mixing syringe assembly, comprising with first and second cartridges of the type having a cartridge barrel with an interior, an open proximal end, a normally sealed distal end and a piston within the interior, the pistons defining variable volume regions within the first and second cartridges within which first and second pharmaceutical components are contained, and further comprising:

a syringe barrel having an interior, open proximal and distal ends, the first and second cartridges at least partially housed within the interior thereof with the distal end of the second cartridge facing the proximal end of the first cartridge, the first and second cartridges being movable relative to one another from a first, pre-mixed position to a second, post-mixed position when the first and second cartridges are in the at least partially housed position within the interior;

means for driving the first pharmaceutical component from the variable volume region of the first cartridge into the variable volume region of the second cartridge to mix with the second pharmaceutical component therein to create a mixed pharmaceutical when the cartridges are in the second, post-mix position;

a dispensing element in fluid communication with the mixed pharmaceutical when the cartridges are in the second, post-mix position;

a drive stem mounted within the syringe barrel for movement therein;

first ratchet means for preventing the drive stem from moving in a proximal direction, that is in the direction from the distal end to the proximal end of the syringe barrel when the cartridges are in the second, post-mix position;

a reciprocating ratchet plunger;

second ratchet means, engaging the drive stem and connected to the ratchet plunger, for driving the drive stem in a distal direction, that is in the direction from the proximal end to the distal end of the syringe barrel, upon movement of the ratchet plunger in the distal direction and when the cartridges are in the second, post-mix position; and the ratchet plunger being movable a distance between a pre-injection position, away from the second cartridge, and a post-injection position, towards the second cartridge;

whereby repeated reciprocal movements of the ratchet plunger between the pre-injection and post-injection positions causes the drive stem to drive the piston of the second cartridge the distance in the distal direction to drive amounts of the mixed pharmaceutical through the dispensing element.

8. The syringe assembly of claim 7 wherein the distal end of the second cartridge passes into the first cartridge through the proximal end of the first cartridge when the cartridges are moved to the second, post-mixed position.

9. The syringe assembly of claim 7 wherein the driving means includes a spike assembly including a double-ended needle adapted to pierce the distal end of the second cartridge and the piston of the first cartridge so to fluidly couple the variable volume regions of the first and second cartridges.

10. The syringe assembly of claim 9 wherein the driving means includes an activation sleeve slidably mounted within the syringe barrel, the second cartridge housed within the activation sleeve for movement therewith.

11. The syringe assembly of claim 10 further comprising means, associated with the syringe barrel, for preventing the unintended movement of the cartridges from the first, pre-mixed position to the second, post-mixed position.

12. The syringe assembly of claim 11 wherein the movement preventing means includes a slot formed in the activation sleeve.

13. The syringe assembly of claim 10 wherein the ratchet plunger is reciprocally mounted within the activation sleeve.

14. The syringe assembly of claim 13 wherein the ratchet plunger includes a bayonet slot means for selectively coupling the ratchet plunger to the second ratchet means.

15. The syringe assembly of claim 13 wherein the ratchet plunger has a length, the ratchet plunger including a dosing key stop positioned at a chosen position along the length, the chosen position determining said distance.

16. The syringe assembly of claim 15 wherein the activation sleeve includes means for preventing access to the dosing key after the ratchet plunger has been mounted within the activation sleeve so to prevent changing the chosen position by the user.

17. The syringe assembly of claim 7 wherein the first cartridge is fixed to the distal end of the syringe barrel.

18. The syringe assembly of claim 7 wherein the first ratchet means is secured to a position adjacent the proximal end of the second cartridge.

19. A method for packaging, dose setting, mixing, and administering repeated equal doses of a multi-component pharmaceutical comprising the following steps:

selecting first and second cartridges, having hollow interiors, needle ends, plunger ends and pistons therebetween, the first and second cartridges containing first and second pharmaceutical within the hollow interiors between the needle ends and the pistons thereof;

mounting the first and second cartridges at least partly within a housing in an axially aligned orientation with the plunger end of the first cartridge opposite the needle end of the second cartridge;

positioning a dose-setting key stop at a chosen position along a user operated ratchet plunger, said chosen position corresponding to said equal doses;

securing the ratchet plunger to the housing with the dose-setting key stop at a user-inaccessible location thereby preventing the user from changing the position of the dose-setting key stop along the ratchet plunger;

forcing the first pharmaceutical from the first cartridge to the second cartridge thereby creating a mixed pharmaceutical; and actuating the ratchet plunger by:
  moving the ratchet plunger in a proximal direction away from the cartridges to a preinjection position determined by the chosen position of the dose-setting key stop; and
  moving the ratchet plunger in a direction towards the cartridges a distance determined by the chosen position of the dose-setting key stop thereby moving the piston of the second cartridge towards the needle end of the second cartridge said distance thereby dispensing one of said equal doses of said mixed pharmaceutical.

* * * * *